United States Patent [19]

Rudner

[11] Patent Number: 4,573,471
[45] Date of Patent: Mar. 4, 1986

[54] PROSTHETIC APPARATUS FOR SURGICAL ANASTOMOSIS

[76] Inventor: Merritt A. Rudner, 4191 NW. 41st St., Apt. #418, Lauderdale Lakes, Fla. 33319

[21] Appl. No.: 629,007

[22] Filed: Jul. 9, 1984

[51] Int. Cl.[4] ............................................. A61B 17/11
[52] U.S. Cl. .................................... 128/346; 128/335; 128/748; 24/569
[58] Field of Search ................... 128/334 R, 335, 748, 128/346, 334 C; 24/279, 535, 569; 411/83

[56] References Cited

U.S. PATENT DOCUMENTS

| | | |
|---|---|---|
| 3,240,207 | 3/1966 | Barker et al. ................. 128/334 R |
| 3,588,920 | 5/1971 | Wesolowski . |
| 3,683,926 | 8/1972 | Suzuki . |
| 3,866,473 | 2/1975 | Teitebaum et al. ................. 24/535 |
| 3,870,092 | 3/1975 | Rusk et al. ................. 411/83 |
| 4,169,477 | 10/1979 | Bokros . |
| 4,182,339 | 1/1980 | Hardy, Jr. . |
| 4,267,842 | 5/1981 | Archibald . |
| 4,306,318 | 12/1981 | Mano et al. . |

OTHER PUBLICATIONS

Austenal Laboratories, Inc. (Surgical Division), *Vitallium Surgical Appliances*, 1948.

Primary Examiner—Richard C. Pinkham
Assistant Examiner—G. Jackson
Attorney, Agent, or Firm—Oltman and Flynn

[57] ABSTRACT

Surgical prosthetic apparatus for joining the ends of organic tubular vessels to be anastomosed consisting of a tubule over which the ends to be joined are drawn, combined with a clamp consisting of two flat parts with a channel between them. The channel is clamped over the tubule by means of screws through the clamp parts, which are drawn together and clamps the walls of the vessel against the outside of the tubule, so that the ends are prevented from sliding apart. The screws may advantageously be locked by means of locking screws. The clamping pressure can be monitored by means of a manometer having a pressure sensing bulb which can be inserted into a cavity formed between the clamp parts.

15 Claims, 9 Drawing Figures

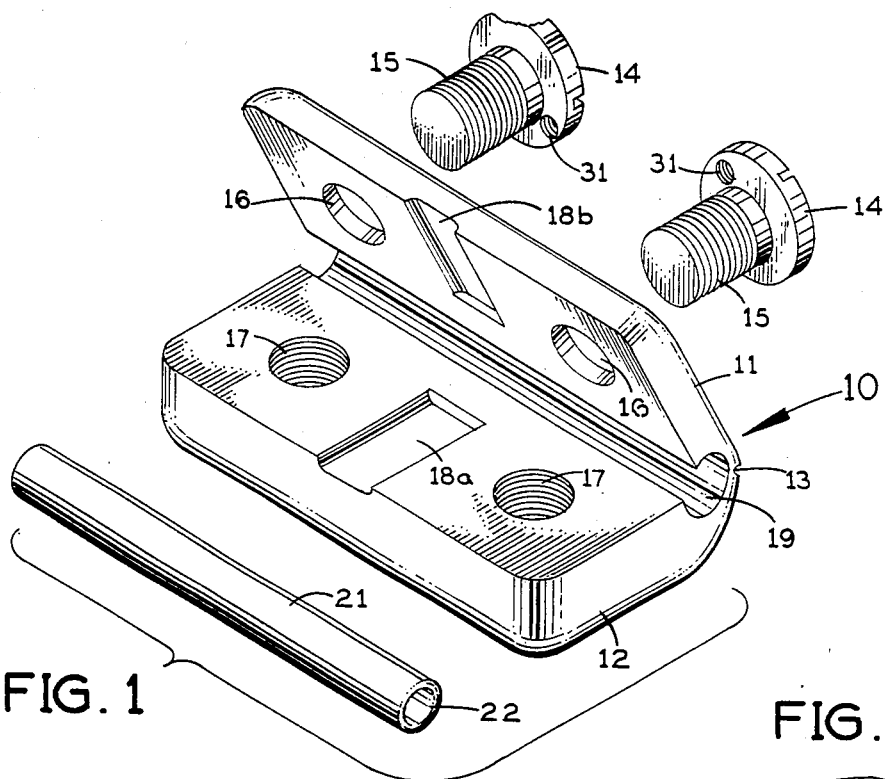
FIG. 1
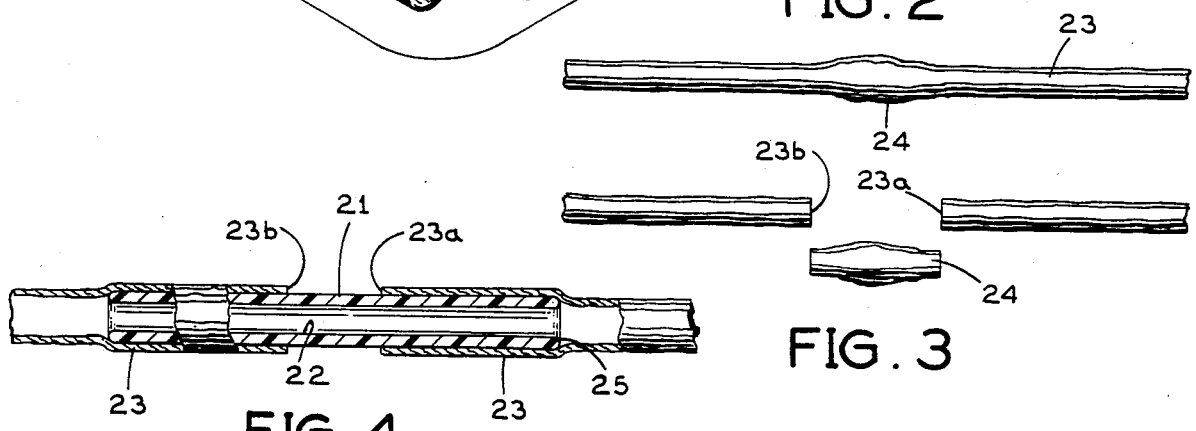
FIG. 2
FIG. 3
FIG. 4
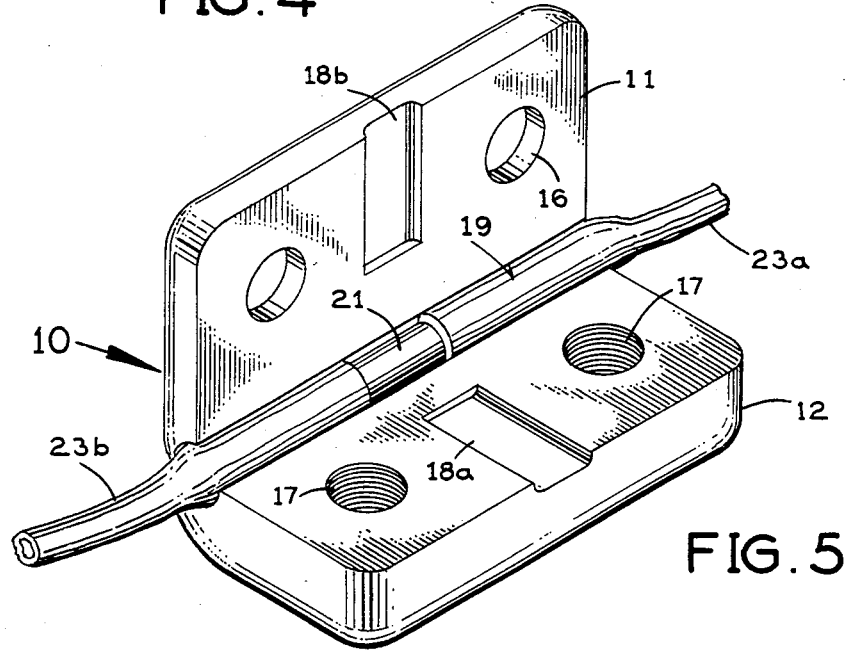
FIG. 5

PROSTHETIC APPARATUS FOR SURGICAL ANASTOMOSIS

BACKGROUND

The invention relates to prosthetic apparatus for performing surgical anastomosis, and more particularly for performing anastomatic surgery for replacing sections of occluded veins and arteries. The prosthetic apparatus is also suited for performing intestinal anastomosis.

Whenever an artery, vein or any other vascular organ becomes occluded or inflamed, it is well known to remove surgically a section of such organ and to replace the removed section with a tubular prosthesis of suitable size for joining the edges of the bisected vessel.

Inventors have in the past sought solutions for joining such severed edges of organic vessels.

U.S. Pat. No. 4,306,318 discloses a tubular organic prosthesis made of polytetrafluoroethylene (Teflon) with helical fibers on its outside.

U.S. Pat. No. 4,267,842 discloses a tubular inner sleeve with an outer sleeve grip mechanism for clamping the ends of an artery.

U.S. Pat. No. 4,182,339 discloses an anastometic device having a pliable sleeve to secure the free ends to be anastomosed by suturing.

U.S. Pat.No. 4,169,477 discloses an anastomatic coupling with an implantable tubular prosthetic device and an outer heat-shrinkable sleeve to provide compressive contact.

U.S. Pat. No. 3,683,926 discloses a soluble connecting tube with tapered ends.

U.S. Pat. No. 3,588,920 discloses a surgical vascular prosthesis made from polyester fiber paper.

SUMMARY

In all the known types of a vascular prosthesis, the surgeon is faced with the task of performing the connecting procedure in a cumbersome way which is time consuming or offers poor accessibility. The present invention overcomes this problem by means of a structure consisting of an inner tubule to be inserted into the mating ends of a bisected vessel and a matching clamp with two hinged parts with a cylindrical channel between the parts that can be closed around the two ends of the vessel joined by the tubule. The clamp can be closed by means of one or two screws through the clamp parts which adjustably enables the surgeon to adjust the amount of pressure applied against the walls of the vessel so that adequate pressure is provided to insure against the ends of the vessel being pulled apart and also so that not too much pressure is applied so that the tissue in the walls is damaged.

In a preferred embodiment of the instant invention a cavity is provided in the space between the clamp parts for receiving a pressure sensing bulb end of a manometer for reading the pressure applied to the clamp parts by the tightening of the screws. The pressure sensing is preferably done by means of a manometer that indicates the pressure in millimeters of mercury on a mercury column in a glass tube. After adjusting the pressure to the proper value the pressure sensing bulb is withdrawn and the screw heads are locked into position by any one of several suitable means, so that the adjustment will not later change as a result of the movements of the internal body parts surrounding the prosthesis.

BRIEF DESCRIPTION OF THE DRAWINGS

FIG. 1 shows, in a perspective view, a tubule for joining the ends of a vessel and an open clamp consisting of two hinged clamp parts to be closed by means of two screws, and also showing the recess for the manometer sensor bulb.

FIG. 2 shows an artery, vein or any other organic tubular body vessel with a fistula.

FIG. 3 shows the body organ of FIG. 2 with the fistula disconnected from the vessel and the two tube ends to be joined.

FIG. 4 shows the two vessel ends joined by a tubule.

FIG. 5 is a perspective view of the two joined ends of the vessel placed in a matching channel in the clamp parts, which are shown in the open condition.

Other objects of this invention will appear from the following description and appended claims, reference being had to the accompanying drawings forming a part of this specification wherein like reference characters designate corresponding parts in the several views.

DETAILED DESCRIPTION OF THE PREFERRED EMBODIMENTS

Figure 6:
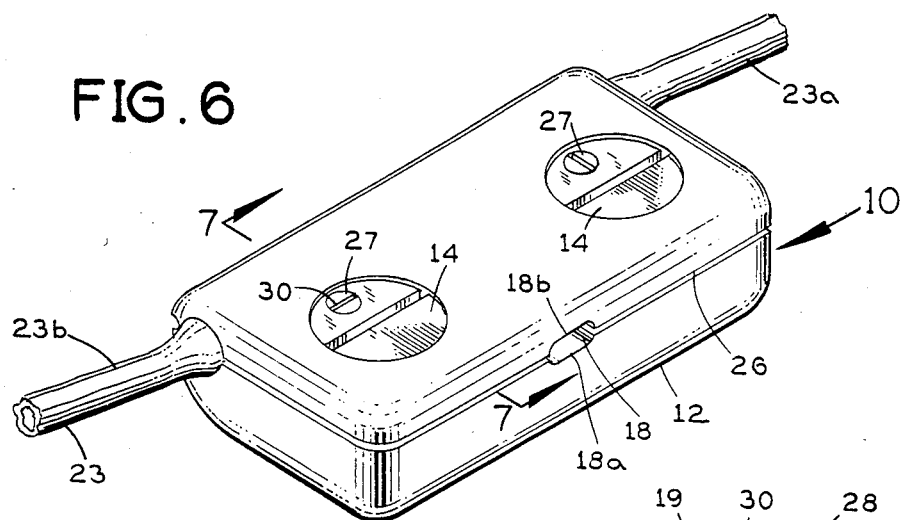
FIG. 6 is a perspective view of the clamp in the closed condition.

Before explaining the disclosed embodiment of the present invention in detail, it is to be understood that the invention is not limited in its application to the details of the particular arrangement shown, since the invention is capable of other embodiments. Also, the terminology used herein is for the purpose of description and not of limitation.

In FIG. 1 the clamp, generally at 10, consists of an upper generally planar clamp part 11 and a lower, also generally planar clamp part 12. The two clamp parts 11, 12 are generally rectangular in shape and are pivotally attached to one another along one of the long edges in a living hinge 13 consisting of a thin, indented flexible section of the same material used for forming the clamp parts. The screws 14, which serve to hold the two clamp parts together have threaded shanks 15 which can be received in smooth clearance holes 16 and matching threaded holes 17.

A cylindrical channel 19 proximal to and parallel with the hinge 13 serves to receive the tubule 21 with the two ends of the tubular vessel to be joined. The tubule has an inner hole 22 which admits blood or any other organic fluid to be transmitted through the tubule.

Two coordinated recesses 18a and 18b in the lower and upper clamp parts 11 and 12 respectively serves to receive the pressure-sensing bulb end of the manometer to be described hereinbelow.

In FIG. 2, an artery, vein or any other tubular vessel shows a fistula 24, which may be an inflamed or occluded section that requires removal.

FIG. 3 shows the fistula 24 removed and the vessel ends, 23a and 23b, that have to be rejoined.

FIG. 4 shows the two ends 23a and 23b joined by means of the tubule 21.

The tubule 21 advantageously has tube end edges that are suitably rounded or "feathered" as shown so that they may readily receive the ends 23a and 23b of the vessel 23 joined by the tubule 21 and inserted into the channel 19 of the open clamp 10. When the two clamp parts 11 and 12 are closed, the channel 19 closes around the ends 23a and 23b of the vessel 23 and clamps them against the outer surface of the tubule 21. The closed assembly is seen in FIG. 6 wherein the upper and lower parts of 11 and 12 form a unitary assembly 10. A small space 26 remains between the two parts 11 and 12 so that the clamping pressure against the walls of the ends of the vessel can be adjusted to the proper value as described hereinabove by the tensioning of the screws 14. A cavity 18 composed of the two recesses 18a and 18b serves to receive the bulb end of a manometer for reading the clamping pressure.

The clamp 10 has rounded corners and edges so that it may fit snugly inside a human body without chafing against adjoining body organs and membranes. The two screws 14 have slots 28 for rotating the screws and the flat head 29 of the screws 14 advantageously has two smaller threaded discs 27, each having a slot 30 and threadedly received in matching threaded holes 31 in the screw heads, best seen in FIG. 7. The discs 27 serve to secure the position of the screws 14 once they have been properly adjusted, so that the screws 14 will not change their position or come loose after insertion into the body.

Figure 7:
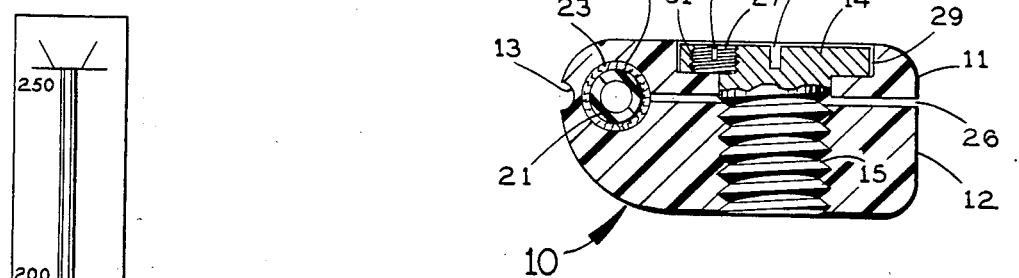
FIG. 7 is a cross-sectional view through the closed clamp holding the vessel and the tubule, seen along the line 7—7 of FIG. 6.

FIG. 7 is the clamp 10 seen in a cross-sectional view taken along the line 7—7 of FIG. 6 showing the tubule 21 surrounded by the walls of the vessel 23 which are clamped in place by the inner walls of the channel 19, and the clamping screw 14 with locking disc 27.

Figure 9:
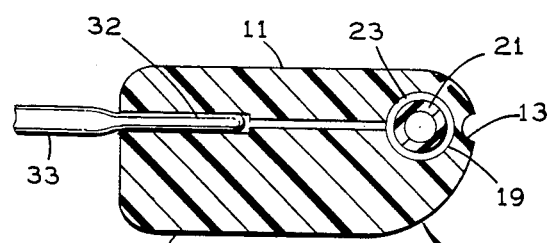
FIG. 9 is another cross-sectional view through the clamp taken along the line 9—9 of FIG. 8.
Figure 8:
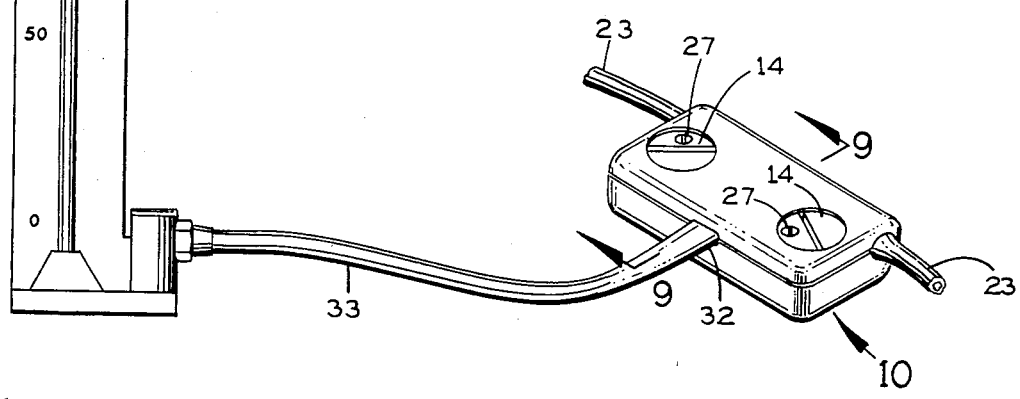
FIG. 8 is a perspective view of the closed clamp holding the vessel and having the pressure sensing bulb end inserted and connected to the manometer.

FIG. 9 is another cross-sectional view through the clamp 10 taken along the line 9—9 of FIG. 8, showing the pressure sensing bulb end 32 of a capillary tube 33 connected to a manometer 34 (FIG. 8) with a viewing glass 35 which shows the pressure against the bulb 32 in millimeters of mercury on a mercury column seen through the viewing glass 35. The pressure against the sensing bulb 32 represents the clamping pressure between the parts 11 and 12 of the clamp 10, exerted by the screws 14.

The clamp 10 and the tubule 21 as well as the associated parts, the screws 14 and the locking discs 27, are made of a nontrombonic plastic material that meets a number of requirements for materials to be inserted into a human body. One material that is well suited is generally known as medical grade polytetrafluorethylene, generally known as teflon, which is well accepted by the human body. The teflon material may advantageously be produced from teflon powder that is formed by molding or extrusion and sintered by heating. It is also elastic and highly stable and resistant to body fluids. It must be manufactured without a plasticizer which could leach out of the material and cause contamination and rejection by the human body. The teflon material described above lends itself well to extrusion according to the following method: First applying a force necessary to press the teflon into the desired shape applying heat from a heat exchanger consisting of four laser beams equally spaced apart around the diameter of the thin wall tubing, or other heating means, used for the tubule 21 and applying a temperature of 600–605 degrees F.; and next extruding the material in a highly polished forming die to create the smoothest finish possible, thereby preventing the formation of plaque from the blood traversing the tube.

The base material may advantageously be made from virgin teflon with no fillers, no reprocessed material, no "Deobase" or other plasticizer, no copolymers, and no commercial solvent such as trichlorethylene.

In a different method of joining the bisected ends of the tubular vessel, the ends of the vessel may be pushed over the ends of the tubule 21 and tied thereto by means of a sterile thread also made by extruding the above-described teflon material, using a suitable tie knot.

The parts used for the clamp 10 may be made by molding or extrusion or machining of the pure teflon material, and then sterilizing it by boiling it in water and packing it in sterile plastic bags containing ethyl alcohol.

The tubule 21 may advantageously be manufactured with an inlet end of the same diameter as the corresponding human tubular vessel, and the outlet end slightly larger, e.g. 0.001" larger which creates a slight venturi effect which further minimizes the formation of plaque when used as a part of a vascular system.

The outside diameter of the tubule 21 will be chosen so that it fits the inside diameter of the channel 19 between the two clamp parts 11 and 12.

I claim:

1. A joining system for the ends of organic tubular vessels to be anastomosed, the system comprising:
   a tubule having an inside diameter substantially equal to the inside diameter of the ends of the vessels to be joined by being drawn over the ends of the tubule;
   a clamp having an open and a closed position, consisting of two substantially planar clamp parts having between them a cylindrical channel for receiving and clamping walls of the ends of the vessel to the outside of the tubule;
   means for drawing together said clamp parts into their closed position; and
   means for monitoring the clamping pressure exerted against the walls of the vessel.

2. A joining system according to claim 1 wherein said clamp parts have a common straight edge, the clamp parts being pivotally joined by said straight edge.

3. A joining system according to claim 2 wherein said edge is a living hinge consisting of an indented flexible membrane formed of the material constituting the clamp parts.

4. A joining system according to claim 3 wherein each of said clamp parts has an inner, substantially planar surface, each of said surfaces intersecting the other surface in the line defining said common straight edge.

5. A joining system according to claim 4 wherein said channel is evenly divided into half parts along its axis between said two clamp parts.

6. A joining system according to claim 5 wherein said channel is substantially parallel with said hinge.

7. A joining system according to claim 6 wherein said means for drawing together said upper and lower clamp parts comprise at least one screw, said screw having a shank with a threaded part and a screw head, said upper and lower clamp parts each having a hole 5 therethrough, said hole oriented with its axis substantially perpendicular to said planar inner surface, said holes colinearly disposed and mutually coordinated to receive said screw, when said clamp parts are in their closed condition.

8. A joining system according to claim 7 wherein one of said holes is threaded for threadedly receiving the threaded part of said screw shank and wherein the other hole is a smooth clearance hole for receiving said screw shank.

9. A joining system according to claim 7 wherein said screw further comprises a locking disc for locking said screw into a locked condition.

10. A joining system according to claim 4 wherein each of said inner planar surfaces has a recess, said recesses mutually coordinated to form a cavity when said clamp parts are in their closed position, and wherein said means for monitoring the clamping pressure is a manometer having a pressure sensitive bulb, said cavity serving to receive said pressure sensitive bulb, the bulb connected to said manometer by a capillary tube.

11. A joining system according to claim 10 wherein said manometer is a mercury column manometer having a pressure range to generally 250 millimeter mercury.

12. A joining system according to claim 1 wherein said upper and lower parts and said tubule is made of medical grade polytetrafluoroethylene.

13. A joining system according to claim 1 wherein the inside diameter of one end of the tubule is slightly less than the inside diameter at the other end of the tubule, thereby creating a slight venturi effect for reducing the formation of plaque from the blood in the tubule.

14. A joining system according to claim 13 wherein said one end of the tubule is the inlet end and the other end is the outlet end.

15. A joining system according to claim 13 wherein the inside diameter of said one end is generally 0.001" less than the inside diameter of the other end.

* * * * *